(12) United States Patent
Kusano et al.

(10) Patent No.: US 8,222,284 B2
(45) Date of Patent: Jul. 17, 2012

(54) STABLE FORMULATIONS OF THIADIAZOLE DERIVATIVE

(75) Inventors: Hiroko Kusano, Tokyo (JP); Dinesh Shyamdeo Mishra, Carmel, IN (US); Yoshikazu Tashiro, Tokyo (JP); Yosuke Watanabe, Tokyo (JP); Hong Zhuang, Zionsville, IN (US)

(73) Assignees: Eli Lilly and Company, Indianapolis, IN (US); Kyowa Hakko Kirin Co., Ltd., Tokyo (JP)

( * ) Notice: Subject to any disclaimer, the term of this patent is extended or adjusted under 35 U.S.C. 154(b) by 406 days.

(21) Appl. No.: 12/665,740

(22) PCT Filed: Jul. 7, 2008

(86) PCT No.: PCT/US2008/069301
§ 371 (c)(1),
(2), (4) Date: Dec. 21, 2009

(87) PCT Pub. No.: WO2009/009470
PCT Pub. Date: Jan. 15, 2009

(65) Prior Publication Data
US 2011/0009458 A1    Jan. 13, 2011

Related U.S. Application Data

(60) Provisional application No. 60/949,268, filed on Jul. 12, 2007.

(51) Int. Cl.
*A61K 31/433*    (2006.01)
(52) U.S. Cl. ........................................................ 514/363
(58) Field of Classification Search .................. None
See application file for complete search history.

(56) References Cited

FOREIGN PATENT DOCUMENTS

| | | |
|---|---|---|
| CA | 2602397 | 9/2006 |
| EP | 1616866 | 1/2006 |
| WO | WO2004/092147 | 10/2004 |
| WO | WO2006/101102 | 9/2006 |

*Primary Examiner* — James D Anderson
(74) *Attorney, Agent, or Firm* — Danica Hostettler

(57) ABSTRACT

The present invention provides formulation parameters and manufacturing conditions for stable pharmaceutical compositions comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide that minimize undesirable chiral conversion to the less active S enantiomeric form.

16 Claims, No Drawings

STABLE FORMULATIONS OF THIADIAZOLE DERIVATIVE

This is the national phase application, under 35 U.S.C. 371, for PCT/US2008/069301 filed Jul. 7, 2008, which claims the priority of U.S. Provisional Application No. 60/949,268 filed Jul. 12, 2007.

The present invention provides formulation parameters and manufacturing conditions for stable pharmaceutical compositions comprising a thiadiazole derivative. In particular, the present invention provides chirally stable pharmaceutical compositions comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide. Stable manufacturing conditions for this compound and intermediates are also provided.

BACKGROUND OF THE INVENTION

The compound N-{4-(2,2-dimethyl-propionyl)-5-[(2-ethylamino-ethanesulfonylamino)-methyl]5-phenyl-4,5-dihydro-[1,3,4]thiadiazol-2-yl}-2,2-dimethyl-propionamide was first described in PCT International Publication Number WO 03/051854. A formulation containing the compound N-{4-(2,2-dimethyl-propionyl)-5-[(2-ethylamino-ethanesulfonylamino)-methyl]-5-phenyl-4,5-dihydro-[1,3,4]thiadiazol-2-yl}-2,2-dimethyl-propionamide is described in PCT international Publication Number WO 2004/092147. A formulation containing the compound N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide is described in PCT International Publication Number WO 2006/101102. This compound is useful, for example, for therapeutic treatment of a human malignant tumor.

Stable formulations of the compound N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide which minimize chiral conversion to the less active S enantiomeric form are desired for reproducible and efficient manufacturing and commercial scale preparation, long-term storage of a lyophilized form, and stability when the lyophilized form is reconstituted and delivered to a patient. Surprisingly, formulation parameters and manufacturing conditions were discovered that provide stable pharmaceutical compositions comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide that minimize undesirable chiral conversion to the less active S enantiomeric form.

SUMMARY OF THE INVENTION

The present Invention provides a pharmaceutical composition comprising N-{4-(2,2-dimethyl-propionyl)-(5R)-5-[(2-ethylamino-ethanesulfonylamino)-methyl]-5-phenyl-4,5-dihydro41,3,41thiadiazol-2yl}-2,2-dimethyl-propionamide, and a pharmaceutically acceptable carrier, diluent, or excipient in solution wherein the pH of said composition is less than 6.4 and greater than 2.0, less than 6.2 and greater than 2,0, less than 5.4 and greater than 2.0, or less than 4.2 and greater than 2.0.

The present invention further provides a lyophilized pharmaceutical composition comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, and a pharmaceutically acceptable carrier, diluent, or excipient wherein the pH of said composition when diluted with aqueous diluent is less than 6.4 and greater than 2 0, less than 6.2 and greater than 2.0, less than 5.4 and greater than 2.0, or less than 4,2 and greater than 2.0.

The present intention also provides a lyophilized pharmaceutical composition comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, and a pharmaceutically acceptable carrier, diluent, or excipient wherein the pH of said composition is less than 6.4 and greater than 2.0, less than 6.2 and greater than 2.0, less than 5.4 and greater than 2.0, or less than 4.2 and greater than 2,0.

The present invention provides a pharmaceutical composition comprising N-{4-dimethyl-propionyl)-(5R)-5-[2-ethylamino-ethanesulfonylamino)-methyl]-5-phenyl-4,5-dihydro-[1,3,4]thiadiazol-2-yl}-2,2-dimethyl-propionamide, and a pharmaceutically acceptable carrier, diluent, or excipient in solution wherein the pH of said composition is less than 6.2 and greater than 2.0, less than 5.4 and greater than 2.0, or less than 4.2 and greater than 2.0 and the temperature of said composition is less than 40° C. and greater than 25° C.

The present invention also provides a pharmaceutical composition comprising {4-(2,2 -dimethyl-propionyl)-(5R)-5-[(2-ethylamino-ethanesulfonylamino)-methyl]-5-phenyl-4,5-dihydro-[1,3,4]thiadiazol-2-yl}-2,2-methyl-propionamide, and a pharmaceutically acceptable carrier, diluent, or excipient in solution wherein the pH of said composition is less than 8.4 and greater than 2.0 and the temperature of said composition is less than 25° C. and greater than 5° C. or equal to 5° C.

The present invention further provides a lyophilized pharmaceutical composition comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-methyl-propionamide, and a pharmaceutically acceptable carrier, diluent, or excipient wherein the pH of said composition when diluted with aqueous diluent is less than 6.2 and greater than 2.0, less than 5.4 and greater than 2.0. or less than 4.2 and greater than 2.0 and the temperature of said composition is less than 40° C. and greater than 25° C.

DETAILED DESCRIPTION OF THE INVENTION

The present invention provides a chirally stable pharmaceutical composition comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, and a pharmaceutically acceptable carrier: diluent, or excipient that has reduced or no conversion to the S enantiomeric form. Pharmaceutical compositions for the present invention include both lyophilized forms and solution forms. Examples of solution forms include a solution form ready for lyophilization and a solution form reconstituted after lyophilization and ready for administration to a patient.

A "pharmaceutically acceptable carrier, diluent or excipient" used herein is a medium generally accepted in the art for the delivery of biologically active agents to patients. Such carriers, diluents, or excipients are generally formulated according to a number of factors well within the purview of those of ordinary skill in the art to determine. One skilled in the art of preparing formulations can readily select the proper processes for preparing the pharmaceutical compositions provided in the present invention. See, e.g., Remington: The Science and Practice of Pharmacy (A. Gennaro, et Al., eds., 19$^{th}$ ed., Mack Publishing Co., 1995)

As used herein, the term "patient" refers to a mammal that is afflicted with, for example, a malignant tumor. The most preferred patient is a human As used herein, the term "stable" refers to a pharmaceutical formulation containing N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide that has reduced or no conversion to the S-enantiomeric form and meets defined, regulatory shelf life specifications for this compound as a marketed product, Compounds of the present invention may be administered systemically, such as intravenously.

In order to improve the chiral stability of N-{4-2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, preferred pharmaceutical compositions involve particular formulation parameters, including particular pH and/or temperature conditions. Preferably, one embodiment of the present invention involves a pH range from less than about 6.4 to greater than about 2.0. More preferably, the pH range is from less than about from less than about 6.2 to greater than about 2.0. Even more preferably, the pH range is from less than about 5.4 to greater than about. 2.0. Still more preferably, the pH range is from less than about 4.2 to greater than about 2.0. Various buffers and/or salts are available to maintain or control the pH range. Such buffers and/or salts are preferably tartrate, phosphate, citrate, mesylate, sodium sulfate, sodium chloride, and the like. One such preferable buffer and/or salt is phosphate. More preferably, the buffers and/or salts are sodium phosphate, tartrate, and citrate. Even more preferably, the buffer and/or salt is sodium phosphate. Still more preferably, the buffer and/or salt is tartrate. When using these pH ranges, buffers, and/or salts, the temperature preferably is less than 40° C. and greater than 25° C.

Preferably, when the range for a pharmaceutical composition of the present invention is from less than about 8.4 to greater than about 2.0, the temperature is from less than about 25° C. to greater than about 5° C. More preferably, the temperature of a pharmaceutical composition with a pH range of less than about 8.4 to greater than about 2.0 is about 5° C.

Pharmaceutical compositions that are in solution prior to lyophilization, lyophilized, and/or diluted with aqueous diluent after lyophilization containing N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide preferably contain no more than 2.0% of the less active S enantiomer. More preferably, the pharmaceutical composition contains no more than 1.5% of the S enantiomer. Even more preferably, the pharmaceutical composition contains no more than 1.0% of the S enantiomer. Still more preferably, the pharmaceutical composition contains no more than 0.5% of the S enantiomer. Even still more preferably, the pharmaceutical composition contains no more than 0.3% of the S enantiomer. Most preferably, the pharmaceutical composition contains no more than 0.2% of the S enantiomer.

FORMULATION EXAMPLE

The following formulation example is illustrative and is not intended to limit the scope of the present invention.

In one vial, combine 10 mg N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, 6.0 mg tartaric acid, and 30 mg mannitol. Using water for injection, q.s. to 5.0 mL. Lyophilize the formulation. When ready for use, reconstitute the vial's contents with 5.0 mL water for injection. For this formulation, the concentration of N-{4-(2,2-dimethyl-propionyl)-(5R)-5-[(2-ethylamino-ethanesulfonylamino)-methyl]-5-phenyl4,5-dihydro-[1,3,4]thiadiazol-2-yl}-2,2-dimethyl-propionamide is 2 mg/mL The pH of the formulation is about 3.0 prior to lyophilization and about 3.1 to 3.2 after reconstitution, Pharmaceutical Composition and Manufacturing Studies

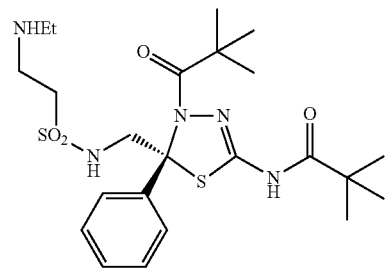

N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide is isolated, for example, as provided in PCT International Publication Number WO 2006/101102 or by utilizing the chiral HPLC assay noted infra.

Stability for N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide (the compound) is assessed at 0.1 mg/mL in various buffers adjusted from pH 2 through 8 with various pH adjusting agents (e.g. 0.1 and 1 N HCl; 0.1, 1, and 5 N NaOH) and at different storage conditions (e.g. 5° C., 25° C., and 40° C. at 75% relative humidity). Hereinafter, the 40° C. at 75% relative humidity storage condition will be referred to as 40° C. These buffers include 10 mM and 50 mM tartrate (40° C.), 10 mM phosphate (25 and 40° C.), 50 mM phosphate (40° C.), and 10 mM citrate (25 and 40° C. Additional solution stability studies include 10 mM citrate (pH 8; 5° C., 25° C., and 40° C.) and 10 mM NaCl, 10 mM sodium sulfate, 10 mM mesylate, 10 mM tartrate, 10 mM phosphate, and 10 mM citrate (pH 8, 40° C). Lyophilized stability studies for N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2-dimethyl-propionamide involve solutions containing 10 mM tartrate buffer at pH 3 which are lyophilized and subjected to storage at 5° C., 25° C., and 40 ° C. for 1, 3, and 6 months. Finally, the enantiomeric stability for N-{4-(2,2-dimethyl-propionyl)-(5R)-5-[(2-ethylamino-ethanesulfonylamino-methyl]-5-phenyl-4,5-dihydro-[1,3,4]thiadiazol-2-yl}-2,2-dimethyl-propionamide is assessed when dissolved in various organic solvents and aqueous/solvent mixtures, including methanol, ethanol, acetonitrile, acetone, ethyl acetate, and 50% ethanol/50% water (all at 25° C. and 40° C.) and in 1-octanol (25° C.).

The achiral stability of the compound is measured using standard reversed-phase HPLC assays. The analytical operating conditions for achiral stability analyses are as follows: Column: Waters XTerra C18 column, 150×4.6 mm, 3.5 micron; Detector: UV, 290 nm; Flow: 0.75 mL/min.; Injection: 10 µL; Column Temperature; 50° C.; Mobile Phase: 50% water with 0.1% TFA/50% acetonitrile with 0.1% TFA.

The enantiomeric stability is measured with a chiral HPLC assay employing polar ionic separation conditions. Those conditions include Column: Chirobiotic T, 150×4.6 mm; Detector UV, 290 nm; Flow: 0.225-0.35 mL/min., adjust to optimize chiral separation; injection: 2 μL-10 μL; Column Temperature: 45° C.; Mobile Phase: 0.01% TEA, 1.0% HOAc, 1.0% water (DIW) in methanol. Enantioselectivity is very sensitive to mobile phase composition, specifically the acid:base ratio. For this reason, the TEA and HOAc additives are accurately measured and then delivered by pipette into the mobile phase while stirring.

In 10 mM and 50 mM tartrate buffers, no chiral conversion of the compound is observed at pH 4,1, 3.1, and 2.1 for at least 96 hours at 40° C. and at pH 3.9, 2.9, and 2.0 for at least 120 hours at 40° C., respectively. Furthermore, for this study in 10 mM tartrate buffer, 97.5% of the compound remains after pH 6.2 at 96 hours at 40° C. and 60.3% of the compound remains after pH 8.7 at 96 hours at 40° C.

In 10 mM sodium phosphate buffer, no chiral conversion of the compound is observed at pH 5.4, 3.4, and 2.3 for at least 120 hours at 40° C. and at pH 5.4, 3.4, and 2.3 for at least 120 hours at 25° C. In 50 mM phosphate buffer, no chiral conversion of the compound is observed at pH 5.0, 3.3 and 2.2 for at least 96 hours at 40° C.

In 10 mM citrate butler, no chiral conversion of the compound is observed at pH 4.2, 3.3, and 2.1 for at least 96 hours at 40° C. and for at least 120 hours at 25° C. In citrate buffer at pH 6.2, 98.2% of the compound remains after 96 hours at 40° C. and 99.9% of the compound remains after 120 hours at 25° C.

In 10 mM citrate buffer at pH 8.4, 95.8% of the compound remains after 24 hours at 25° C. and 99.3% of the compound remains after 120 hours at 5° C.

For lyophilized formulations at pH 3.0, no chiral conversion of the compound is observed at 1, 3, and 6 months for 5° C., 25° C., or 40° C. storage conditions.

In general, N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide is less stable and, thus, converts more readily to the S enantiomeric form in acetonitrile, ethyl acetate, and 50% ethanol/50% water than in the other solvents that are tested.

We claim:

1. A pharmaceutical composition comprising N-{4-(2,2-dimethyl-propionyl)-(5R)-5-[2-ethylamino-ethanesulfonylamino)-methyl]-5-phenyl-4,5-dihydro-[1,3,4]thiadiazol-2-yl}-2,2-dimethyl-propionamide, a buffer and/or salt selected from tartrate, phosphate, citrate, mesylate, sodium phosphate, and sodium sulfate, and a pharmaceutically acceptable carrier, diluent, or excipient in aqueous solution wherein the pH of said composition is less than 5.4 and greater than 2.0 and contains no more than 2.0% N{4-(2,2-dimethyl-propionyl)-(5S)-5-[(2-ethylamino-ethanesulfonylamino)-methyl]-5-phenyl-4,5-dihydro-[1,3,4]thiadiazol-2-yl}-2,2-dimethyl-propionamide and is stable to chiral conversion.

2. The pharmaceutical composition of claim 1 wherein the buffer and/or salt is selected from tartrate, phosphate, citrate, and sodium phosphate.

3. The pharmaceutical composition of claim 2 wherein the buffer and/or salt is selected from tartrate and sodium phosphate.

4. The pharmaceutical composition of claim 3 wherein the buffer and/or salt is tartrate.

5. The pharmaceutical composition of claim 1 wherein the pH of said composition is less than 4.2 and greater than 2.0.

6. The pharmaceutical composition of claim 2 wherein the pH of said composition is less than 4.2 and greater than 2.0.

7. The pharmaceutical composition of claim 3 wherein the pH of said composition is less than 4.2 and greater than 2.0.

8. The pharmaceutical composition of claim 4 wherein the pH of said composition is less than 4.2 and greater than 2.0.

9. A lyophilized pharmaceutical composition comprising N-{4-(2,2-dimethyl-propionyl)-(5R)-5-[(2-ethylamino-ethanesulfonylamino)-methyl]-5-phenyl-4,5-dihydro-[1,3,4]thiadiazol-2-yl}-2,2-dimethyl-propionamide, a buffer and/or salt selected from tartrate, phosphate, citrate, mesylate, sodium phosphate, and sodium sulfate, and a pharmaceutically acceptable carrier, diluent, or excipient wherein when diluted with aqueous diluent affords a solution formulation having a pH less than 5.4 and greater than 2.0 and contains no more than 2.0% N-{4-(2,2-dimethyl-propionyl)-(5S)-5-[(2-ethylaminoethanesulfonylamino)-methyl]-5-phenyl-4,5-dihydro-[1,3,4]thiadiazol-2-yl}-2,2-dimethyl-propionamide and is stable to chiral conversion.

10. The lyophilized pharmaceutical composition of claim 9 wherein the buffer and/or salt is selected from tartrate, phosphate, citrate, and sodium phosphate.

11. The lyophilized pharmaceutical composition of claim 10 wherein the buffer and/or salt is selected from tartrate and sodium phosphate.

12. The lyophilized pharmaceutical composition of claim 11 wherein the buffer and/or salt is tartrate.

13. The lyophilized pharmaceutical composition of claim 9 wherein the pH of the solution formulation is less than 4.2 and greater than 2.0.

14. The lyophilized pharmaceutical composition of claim 10 wherein the pH of the solution formulation is less than 4.2 and greater than 2.0.

15. The lyophilized pharmaceutical composition of claim 11 wherein the pH of the solution formulation is less than 4.2 and greater than 2.0.

16. The lyophilized pharmaceutical composition of claim 12 wherein the pH of the solution formulation is less than 4.2 and greater than 2.0.

* * * * *